United States Patent [19]

Bennett

[11] Plant 5,070

[45] Jul. 19, 1983 ost

[54] MINIATURE ROSE PLANT

[76] Inventor: Cecilia L. D. Bennett, 489 Minot Ave., Chula Vista, Calif. 92010

[21] Appl. No.: 344,538

[22] Filed: Feb. 1, 1982

[51] Int. Cl.[3] ..... A01H 5/00

[52] U.S. Cl. ..... Plt./9

[58] Field of Search ..... Plt./7, 9

*Primary Examiner*—Robert E. Bagwill

[57] ABSTRACT

The subject of present disclosure is a new and distinct variety of miniature rose plant characterized by the medium pink, heavily veined in a deeper shade of pink.

1 Drawing Figure

The present invention relates to a new and distinct variety of hardy, dwarf, bush plant of the miniature class; the variety being primarily characterized as a medium pink, similar in coloring to Perfume Delight, a HT. variety introduced in 1973 by Weeks.

The variety is further characterized by:

The veining through the petal of a much deeper shade of pink.

The leaflettes are almost round in shape.

The plant is low growing, compact and well foliaged. The foliage is small, medium green, very serrated with no change of coloring on the edges of the leaflets. The bloom is similar in coloring to Perfume Delight. A medium pink with the exception that it is heavily veined in a deeper shade of pink when grown in the Chula Vista area. During the hot weather it can produce blooms of a lighter shade.

The plant ranges in size from 12–15 inches, will grow slightly taller when grown in the ground.

The present variety of miniature rose was originated by me at Tiny Petal's Nursery located at Chula Vista, Calif., under careful observation, and is a cross of "Little Chief" a miniature as the pollen parent and "Electron" a hybrid tea (U.S. Plant Pat. No. 3,226.) as the seed parent.

Subsequent to origination of the variety I successfully reproduced it by cuttings and bud-grafting at Tiny Petal's Nursery located at aforesaid, with reproductions coming true in all respects.

The color photographs illustrate the variety.

Referring now specifically to the new and distinct variety of miniature rose plant, the following is a Detailed description thereof in outline; all major color plate identification being by reference to The British Colour Council Horticultural Colour Chart.

Type: Hardy, dwarf, rounded; seedling; greenhouse; outdoors; cut flowers; garden decoration; potted plant.

Class: Miniature.

*Variety name.*—"Georgette".

Flowers borne: Usually one to a stem or in clusters of three to five to a stem.

Quantity of bloom: Abundant inside and outside the hothouse or outdoors.

Bud:

*Peduncle.*—Slender; erect; very slight tinge of red; $1\frac{1}{2}''$ to $1\frac{3}{4}''$ in length.

*Hairs.*—Very minute.

*Before calyx breaks.*—Size small.

*Form.*—Short; and with no foliating on appendages. Appendages barely clearing tip of bud.

*Color.*—Medium green with a very faint tinge of red.

*As calyx breaks.*—Color — medium pink with a slight greenish tinge at the base.

*Opening.*—Opens well in all weather.

Bloom:

*Size when fully open.*—Medium, averaging about $1\frac{1}{2}''$ to $1\frac{3}{4}''$. Petalage — double — averaging about 35 to 40 petals, arranged regularly.

*Form.*—High centered circular form. Opens slowly, petals reflex slightly. Open flower reveals stamens.

Petals: Thin; medium substance; matt surface on inside and outside surface of petals.

*Shape.*—Outside petals, broad lanceolate, rounded on the edge; intermediate petals, broad lanceolate, rounded on the edges; inside petals, arrow shaped with rounded edges.

Color: Newly opened flowers from a plant grown at Chula Vista, Calif.:

*Outside petals.*—Outside surface — Phlox pink 625/3 with splash of 625 at base of petal. Page 77 of the British Colour Council Horticultural Colour Chart. Tipped at the base with yellow.

*Outer petals.*—Topside surface — phlox pink 625/2 page 77 with veining of 625 page 77.

*Intermediate petals.*—Outside surface — 625/2 page 77 tipped at the base of petal with yellow.

*Intermediate petals.*—Topside surface — phlox pink 625/2 page 77 with veining of 625 page 77. Base of petal tipped with yellow.

*Inner petals.*—Outside surface — phlox pink, 625/1 page 77 with yellow tip at base of petal.

*Inner petals.*—Upper surface — 625/1 page 77 with veining of 625 page 77.

Behavior: Opens well in all weather. Good form;

*Color.*—Long lasting.

*Flower longevity.*—Cut flowers at room temperature last 5 to 7 days. Outside in the sun, 7 to 10 days depending on the temperature.

Reproductive organs:

*Stamens.*—Abundant, arranged evenly around pistil.

*Filament.*—Varying lengths, short, soft orange with yellow toward the base.

*Anthers.*—Well formed: yellow.

*Pollen.*—Generous amount.

*Pistils.*—20 to 25.

*Styles.*—Short, irregular, color greenish.

*Ovaries.*—All enclosed in calyx.
*Hips.*—Some.
*Sepals.*—Spear shaped; recurved.
*Seed.*—A few.

Foliage:
*Leaves.*—Compound of five, three below the bloom. Fairly small: glossy.
*Leaflets.*—Shape: broad, round, base rounded. Margin very serrated.
*Color.*—All over medium green; new growth medium green, no change of color on margin.

Rachis: Medium length; underside sparsely thorny, otherwise smooth.
*Stipules.*—Medium length; narrow to medium width; narrow points with a slight recurving.

Growth:
*Habit.*—Dwarf; bushy; rounded; much branched.
*Growth.*—Vigorous.
*Canes.*—Medium; slender; sturdy.
*Main stem.*—Color: medium green.

*Thorns.*—Small; slender; hooked slightly downward; reddish.
*Prickles.*—None.
*Branches.*—Color: medium green.
*Thorns.*—1 or 2 between branches; medium length; thin; slight downcurve.

The miniature rose plant and its flowers as herein described may vary in slight detail due to climatic, soil and cultural conditions under which the variety may be grown; the present description being of the variety as grown at Chula Vista, Calif.

I claim:

1. A new and distinct variety of miniature rose plant of hardy, dwarf, bushy, much branched habit, substantially as illustrated and described, characterized by buds and flowers similar in coloring to the variety Perfume Delight a hybrid tea; and further characterized by a low growing; compact plant of miniature proportions.

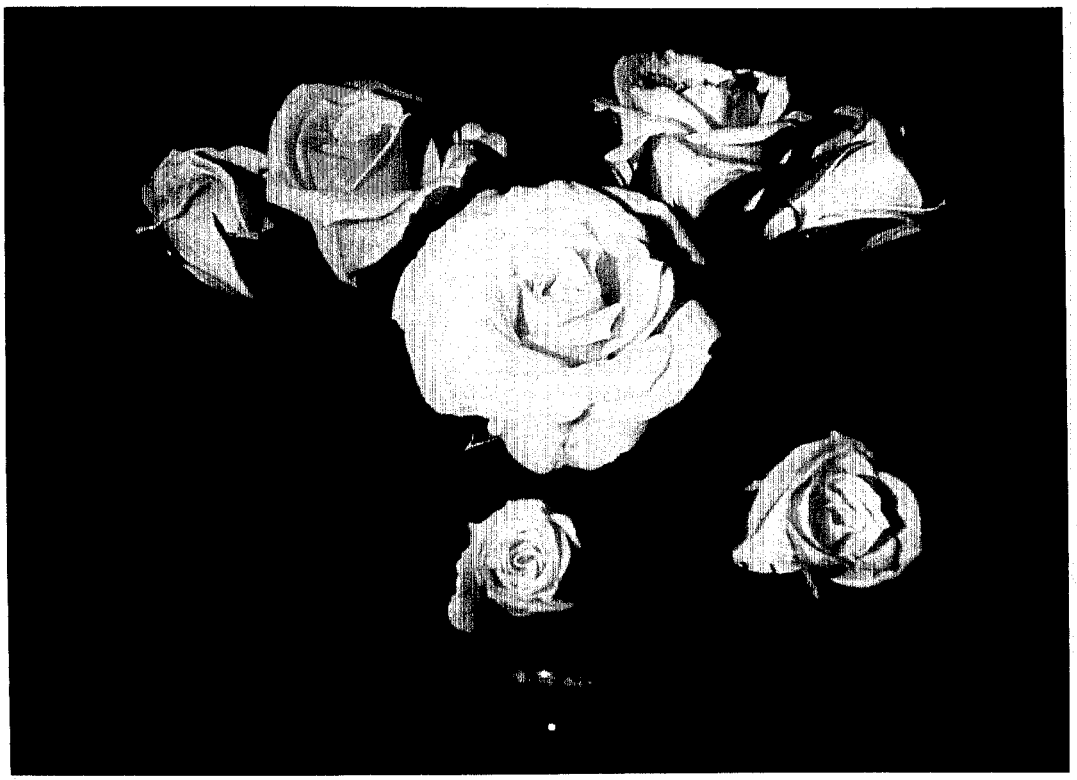

* * * * *